United States Patent [19]
Assenheim

[11] Patent Number: 5,666,061
[45] Date of Patent: Sep. 9, 1997

[54] APPARATUS AND METHOD FOR MEASUREMENT OF MOISTURE CONCENTRATION IN GRANULAR MATERIALS

[75] Inventor: Jerald G. Assenheim, London, England

[73] Assignee: James Instruments Inc., Chicago, Ill.

[21] Appl. No.: 336,858

[22] Filed: Nov. 9, 1994

[51] Int. Cl.⁶ ........................ G01R 27/00
[52] U.S. Cl. ............ 324/636; 324/634; 324/643; 73/159
[58] Field of Search .............. 324/636, 634, 324/643, 635; 73/159

[56] References Cited

U.S. PATENT DOCUMENTS

| | | | |
|---|---|---|---|
| 4,297,874 | 11/1981 | Sasaki | 324/634 |
| 4,829,233 | 5/1989 | Flemming | 324/636 |
| 4,890,054 | 12/1989 | Maeno | 324/636 |
| 5,397,993 | 3/1995 | Tews | 324/634 |

*Primary Examiner*—Kenneth A. Wieder
*Assistant Examiner*—Jose M. Solis
*Attorney, Agent, or Firm*—Michael, Best & Friedrich

[57] ABSTRACT

The measurement of moisture content in granular materials is ordinarily a difficult measurement to make. The invention of this application sets forth a new method and apparatus for measuring moisture content in a wide variety of materials by means of application of an apparatus that makes measurement of moisture content independent of density of the material measured, and thereby unaffected by ambient conditions. The apparatus also allows the practitioner of this invention to readily and accurately measure moisture content.

11 Claims, 3 Drawing Sheets

APPARATUS AND METHOD FOR MEASUREMENT OF MOISTURE CONCENTRATION IN GRANULAR MATERIALS

The invention concerns an apparatus and method of use of same for the purpose of measuring moisture in a variety of industrial materials, independent of a determination of the density of such materials.

SUMMARY OF THE INVENTION

This invention is directed to apparatus for the measurement of moisture in granular material using high frequency waves, such as microwaves, which is comprised of a resonator which is in contact with the material to be measured. The apparatus is further equipped with a means for producing an electromagnetic field that is directed to pass through the material which is to be evaluated for moisture. There is also provided a square wave generator, having an output that is passed through a triangle wave generator, which in turn emits waves which are passed through a high frequency generator, that in turn generates high frequency or microwaves. The high frequency waves are in the range of about 0.5 to about 20 gigahertz.

In addition there are also provided means for determining the natural frequency of the resonator and the resonator when it contains or is in contact with the material to be tested. There is also a high frequency diode for measuring the amplitude of voltage output from the resonator with and without the material being in contact with the generator.

The apparatus also includes detection means for measuring the frequency shift and height of the peak voltage output of the resonater with the material being tested.

Finally, the apparatus may be further comprised of a means (circuit) for converting the output of the resonator into pulse form when the resonator is operated in conjunction with the material to be tested. This calculation may be further processed through a calculating device such as are well known in the art, to derive the percentage of moisture in the material tested, and the results of such calculation displayed in digital or analog form.

DETAILED DESCRIPTION OF THE DRAWINGS

BACKGROUND OF THE INVENTION

Figure 1:
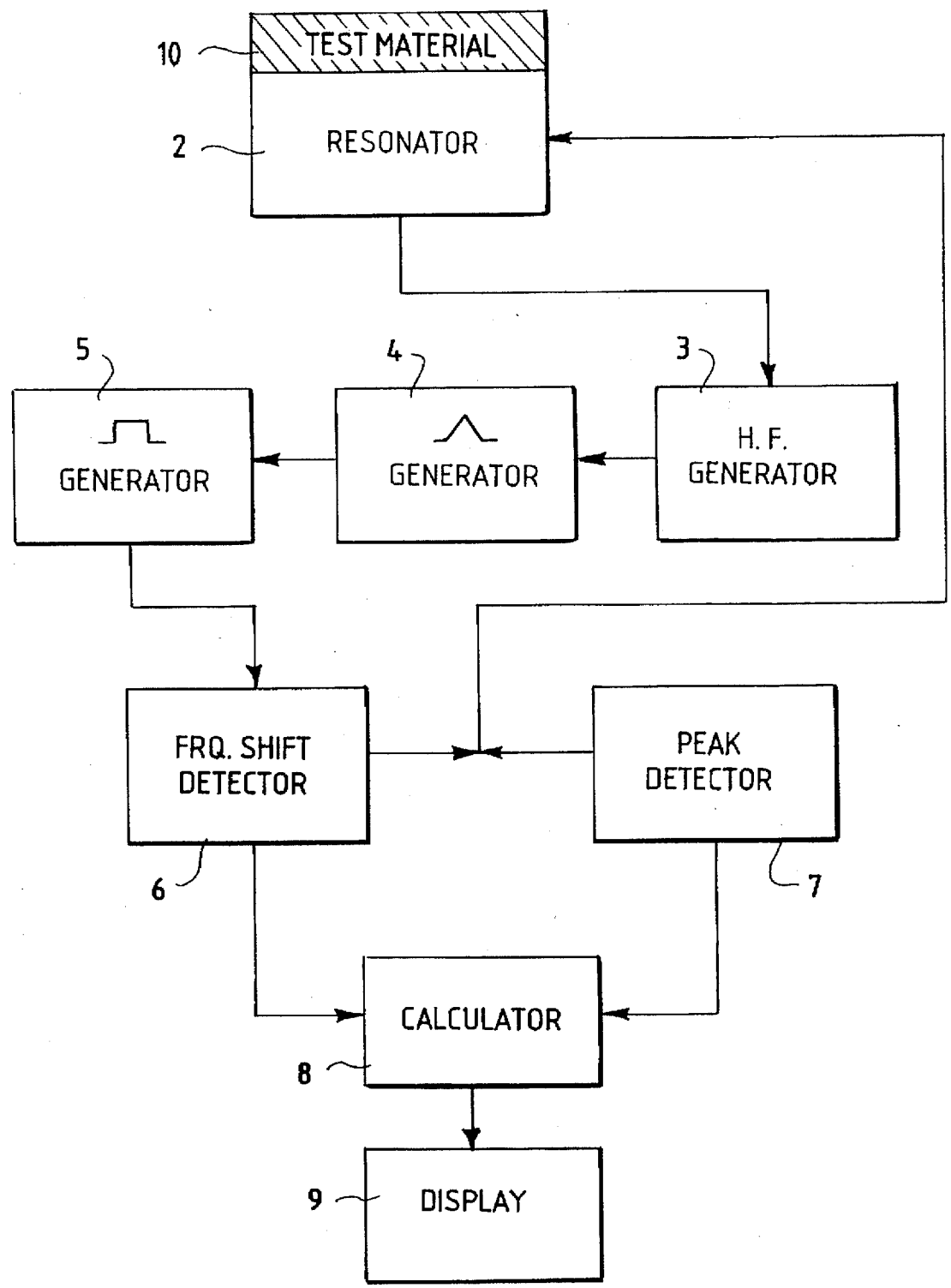
FIG. 1 is a schematic diagram of the various components that comprise the completed apparatus.

Industrial materials that are incorporated into a variety of applications often must be measured precisely in order to ensure a good final product. One of the most crucial components of any industrial material used in fabrication of goods is moisture content. The measurement of moisture present in solid materials seems to be one of the most elusive of all.

Many industrial applications use granular materials, such as sand. These materials often absorb or adsorb water onto the surface of the grains of material. In addition, water may be trapped within the matrix defined by the granular substances. By this means, the difficulty of measuring the water content of the granular material may be increased when traditional methods of measurement are used due to increased drying time. Drying time is dependent upon the number and types of pores in a material, the surface structure of the individual component of a material and the like.

Until now, the only certain measurement of water present is to first weigh and dry out the material. Then, after the material is thoroughly dried, the dried material is weighed and the difference between the moist and dry weights is taken. Unfortunately, this method requires a great amount of time (up to 36 hours and more), and may not yield the same result for the totality of material selected for incorporation into an industrial composition. Despite the difficulties in measurement, the amount of moisture in a given product may be critical to the performance of the material.

A simple example is immediately obvious, and that is measurement of the amount of moisture in the component parts of concrete. Concrete is made of cement, water and a granular aggregate such as sand. The moisture content of sand and aggregate directly affects the performance of the resulting concrete. If the aggregate or sand includes too much water, then the resulting product will not perform as required for certain applications.

In addition, there are innumerable applications for measuring moisture in granular products wherein the resulting finished product may be adversely affected by moisture content of the constituent parts. These products include construction materials, foodstuffs, cosmetics, repair materials and the like.

The classical method of measurement of moisture encompasses the measurement of the weight of the wet basis being compared with the dry weight of the material. The percentage of moisture is, by classical basis according to the "wet" measurement, equal to the weight of water divided by the weight of water plus the weight of material. According to the "dry" basis, the moisture percentage is equal to the weight of water divided by the weight of the dry material.

The two calculations may provide quite different results for the same material and conditions. For example, a 50% moisture content according to the wet basis will indicate a 100% moisture content on the dry basis. While it is not possible to get more than 100% moisture content on the wet basis, materials that can hold more than their own weight of water will give readings of several hundreds or even thousands of percent of moisture on the dry basis. Consequently, an instrument calibrated according to one of the definitions will give a result quite different to an instrument calibrated according to the other. This discussion does not even consider the amount of moisture based upon the volumetric measurement of moisture content.

In industrial processes, any method that ensures the proper measurement of moisture content in what is ordinarily a "dry" i.e., non-liquid phase, wherein the measurement can be conducted on-line, are the most useful. The possible methods of measurement of moisture content vary with the industrial process.

The most direct methods of moisture content, such as chemical methods, may be neither cost effective nor accurate where a material may have variations in moisture content between one portion of material and the next. Large lots of material may, for example, have been exposed to variations in weather or humidity as would occur in a stockpile. The innermost portion of a stockpile may have little or no moisture from the environment whereas the outermost portion may have a great amount of moisture from the atmosphere.

One commonly used method of measurement of moisture is the measure of electrical resistance, or its reciprocal, electrical conductivity. When measuring the resistance, at least two electrical conductors are placed in contact with the wet material and a measure of the conductivity or resistance is taken. The degree of moisture present is estimated from the change in resistance.

This approach has drawbacks as many materials can conduct electricity better than water. Water does not conduct electricity at all unless it contains certain impurities. Water conducts electricity when it contains impurities such as salts, (even in small quantities) so that such measurement of moisture may be, in fact, only a measurement of the impurities in the moisture in a material, rather than the total moisture content.

Other methods have used a simple microwave absorption to calculate the total mount of moisture in a material. The density of the material affects the result. The material in conventional microwave measurement of moisture, measures the heat imparted to the material that is measured, as moisture subject to microwave radiation results in heating. It is only the moisture in materials which causes the heating in conventional microwave cooking, for instance.

Use of low power microwaves eliminates any significant heating of the material to be measured. The conventional application of microwave measurements requires that density be separately measured and allowed for. The density may be easily determined, but may not be accurate throughout a material that is not homogeneous.

Conventional microwave measuring systems typically make use of two sensor heads in the system, one to radiate the beam and one to receive it, which is inconvenient for several reasons. Because the energy has to be transmitted in the form of a narrow beam, some form of focussing device is necessary. This requires a horn or parabolic dish the dimension of which are determined by the frequency in use. This limits the range of frequency which must be high if the size of the resonator is not to become inconveniently large. The two horns for transmitter and receiver must be accurately aligned and thereafter not moved if the calibration is not to change. There is a certain spillage of radiation which has to be screened since it can interfere with other equipment. This radiation can be reflected off of external objects giving spurious readings and generating standing waves which can cause inaccuracies.

In addition, it may not be desirable to heat a material that is being measured. Conventional microwave measurements resulting in heating of the material may cause the material to degrade during the measurement process. Use of low power microwaves eliminates the heating of the material to be measured.

Conventional measuring systems incorporating microwave technologies generally require that density be separately measured and allowed for. The density may be easily determined, but may not be reliable throughout material that is not homogeneous. In addition, the measurements may be highly variable in the event ambient conditions vary with parts of material selected.

The present invention allows the use of an electronic method for measurement of the material and moisture content, and through allowing for density at the time of measurement, results in the attainment of moisture content at the same time as density, but without a separate measurement for density. Such a measurement system also results in differences in microwave absorption for various densities of materials being merged into a value independent of the density. Thus, the moisture content of material may be determined without the determination of density.

There are basically two methods currently in use for measuring moisture using microwave absorption. In one form of instrument a microwave generator feeds a radiating horn or other device for focussing the energy into a narrow beam. This is constrained to pass through the sample under teat after which it is measured by concentrating the beam through a similar horn and applying it to a sensitive receiver tuned to the frequency of the microwave source. The loss of amplitude which occurs when the beam passes through the sample is due to the absorption of energy by the water molecules and can be measured by the receiver. This loss of amplitude is a function of the moisture content of the material tested.

The use of two sensor heads in this system, one to radiate the beam and one to receive it, is inconvenient for several reasons. Because the energy has to be transmitted in the form of a narrow beam, some form of focussing device is necessary. This requires a horn or parabolic dish, the dimensions of which are determined by the frequency i use. This limits the range of frequency that is usable in the system. In thses cases, the frequencies used must be high if the size of the resonating device is not to have an inconveniently large size. The two horns for trnasmitter and receiver must also be accurately aligned and thereafter, not moved so as not to affect the calibration of the device. There is a certain spillage of radiation from these more conventional devices which also must be screened, since it can interfere with the measuring itself, as well as interfere with other equipment. The spilled radiation is also a source of spurious readings and may generate standing waves that can cause inaccuracies in measurement.

It is for these stated reasons that an alternative system using a single head resonator comprising a high frequency resonator which produces an electromagnetic field interacting with the sample material is sometime used. The field produced does not have to be focussed and the system enables lower frequencies to be used which reduce the risk of standing waves. Further, it is desireable for the system to work in a manner that the relaxation time of the water molecules is such as to enable them to respond to the electromagnetic field. The principle thus used is to provide a resonant system which may be in the form of a cavity resonator, or may be made from various types of stripline or micorstrip circuitry.

The moisture in the material under test absorbs energy from the field as imparted by the resonator which lowers the Q factor of the resonator. This can be interpreted in terms of the percentage moisture in the sample as is further discussed herein.

It can be shown that moist materials exhibit a complex dielectric constant which has real and "imaginary" components. Moreover, it has also been shown that for many materials there is a direct relationship between the ratio fof the two parameters fo the complex dielectric constant and the density of the sample material. In measurement, it is generally required, when using conventional applications of microwave measurement, to account for both the density of the material as well as the dielectric constant. The present invention allows the practitioner to measure moisture without having density affect the integrity of the resulting data. In a sense, the measurement method resolves into measuring both the attenuation coefficient and the phase constant of an electromagnetic wave being radiated through the moist material.

Alternatively, where a conventional resonant system is used, the small frequency change at resonance is determined as well as the change in Q factor when energy is absorbed from such a system by moisture. This system results in measurement of the attenuation coefficient alone.

DETAILED DESCRIPTION OF THE INVENTION

The disadvantages and inherent inaccuracies in the standard methods and applications of moisture measurement provided the impetus for the instant invention. The invention is an apparatus and method using a single head comprising a high frequency resonator which produces an electromagnetic field interacting with the sample material. The field does not have to be focussed and the system enable lower frequencies to be used which reduce the risk of standing waves and at which the relaxation time to the water molecules is such as to enable them to respond to the electromagnetic field.

Referring to FIG. 1, the apparatus of this invention comprises a test material 10 that is positioned in relationship to a resonator 2. The resonator 2 receives the output of a high frequency generator 3 which transmits output of a square wave generator 5. The output of the square wave generator 5 is further processed through a triangle wave generator 4 before passing through the high frequency generator 3.

The output of the high frequency generator 3 is also referred to as the swept frequency because the frequency of the electromagnetic wave in the form of a triangular wave is alternately increased and decreased between about 0.5 gigahertz and about 2 Gigahertz. This swept frequency also includes the natural resonant frequency of the resonator.

The resulting output reading from the resonator 2 is then processed through means for detecting frequency shift 6 and through a "Q" measuring circuit or peak detector 7. The results of these two operations are then further processed through the moisture calculation step 8 which may be conducted by simple computation in accord with processes that are known in the art. The results of the moisture calculation 8 step can then be transmitted to the desired display 9.

The steps that are described herein involve equipment and materials that are well known in the art.

Figure 2:
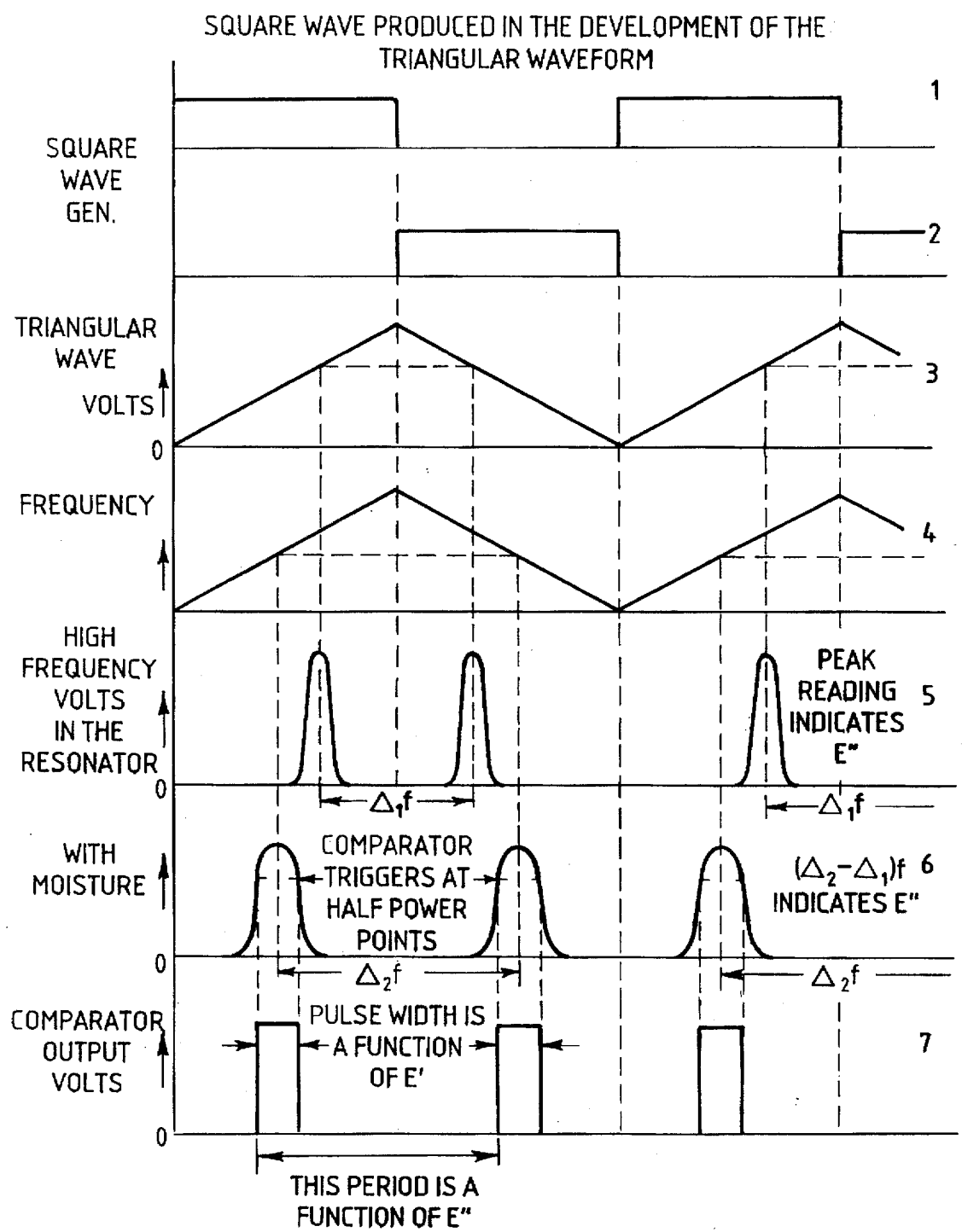
FIG. 2 is a table showing the change in frequency and variety of wave formes and measurements that are accomplished in the practice of the invention.

The steps of the apparatus and method for use are further explained by the schematic diagram/table found in FIG. 2. This FIG. 2 shows the variety of wave forms and measurements that are accomplished in the practice of the invention. The term change in frequency is set forth as "$\Delta f$," where $\Delta$ represents the change and "f" represents frequency.

The principle used is to provide a resonant system which may be in the form of cavity or may be made from various types of stripline or microstrip circuity. Leakage of the fields is allowed to occur and this links with the test material. The moisture in the material under test absorbs energy from this field which lowers the Q factor of the resonator. This can be interpreted in terms of the percentage moisture in the sample.

It can be shown that moist materials exhibit a complex dielectric constant which has real and imaginary components. Moreover, it has also been shown that for many materials there is direct relationship between the ratio of the two parameters of the complex dielectric constant and the density of the sample material. Errors have occurred due to the failure to allow for this variation in density of the industrial moisture measurement in the past. By utilizing a method of measurement whereby the two parameters of the dielectric constant are both separately measured the density may be calculated and allowed for in the measurement and considerably greater accuracy can be obtained. Moreover, much greater freedom in the type of material that can be evaluated is possible using this invention as the operator does not need to recalibrate the instrument for each different sample material, for which different densities may be operative. In addition, recalibration is not required for measurements taken in materials that may have variations in densities due to variation within lots of materials.

The present application is concerned with determining the moisture content of the material without determining every density of each material measured. The dielectric constant of a material containing moisture depends upon both the permitivity of the water and also the permitivity of the material containing the water and by measuring the complex permitivity the of the mixture, the moisture content may be easily calculated in a way which may be independent of the density over a wide range.

PREFERRED EMBODIMENT

In the present invention, a relatively simple apparatus and method of using that apparatus is proposed to determine the phase constant by means of a very sensitive system for the measurement of small changes in the frequency of a resonant system coupled with the material containing moisture. The resonant system may be a resonant cavity but can consist of a suitable resonant section of stripline circuitry. It is necessary that the system produces an electromagnetic field and that this field is constrained to pass through the material containing the moisture to be measured such that the material absorbs energy from the resonant system. The interaction of the field with the moisture causes a change in the "Q" factor of the resonator. The "Q" factor of the resonator is a function of the amount of moisture in the sample.

The presence of a moist sample absorbs energy from the system and therefore lowers the "Q" factor or magnification of the system.

Figure 3A:
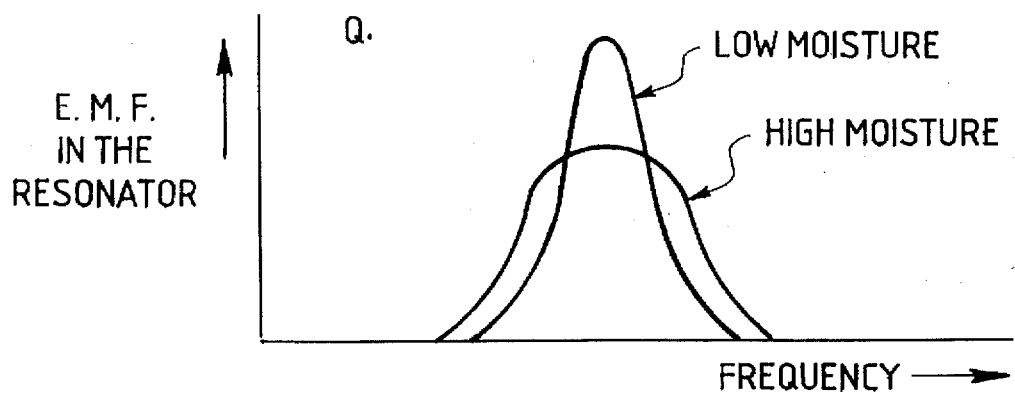
FIG. 3 is a graphical representation of the change in the Q factor in the practice of this invention.
Figure 3B:
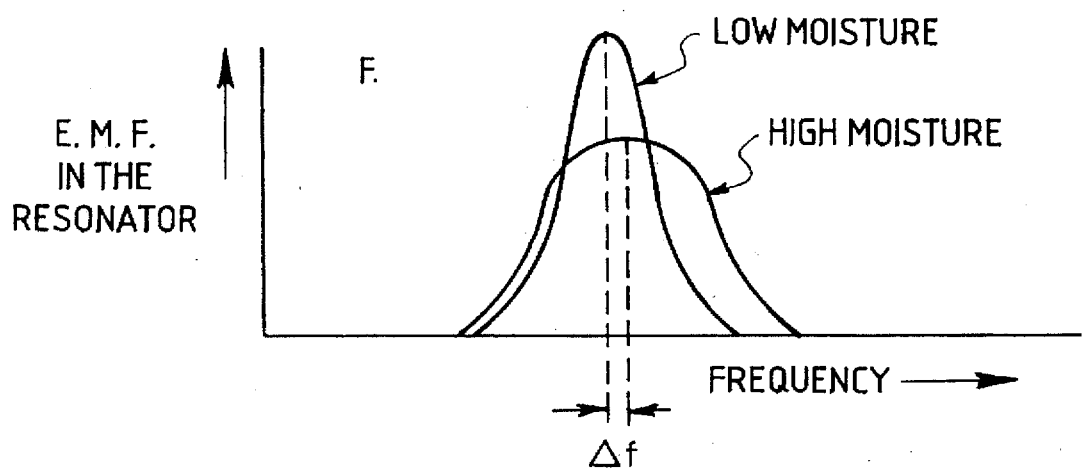

In addition the imaginary or quadrature component produces a reactive effect which causes a slight change in the frequency to which the resonator is tuned as well as a change in the Q factor. The conditions therefor, prevailing when a moist sample is in proximity with the field produced by the resonator are shown in diagrams of FIG. 3.

The proposed system utilizes a method of sensing this frequency change and converting this into a time period and thence into a suitable voltage which may be used along with the Q measurement to calculate the moisture in a way which ignores any change in the density of the sample material. The method involves generating a triangular voltage wave and using this to sweep the frequency of the microwave generator in a linear manner by means of a varactor diode. The frequency is swept through the range covered by the resonator for the range of moisture to be measured and the resonator used for sensing moisture is then swept through its resonant frequency twice in each scan or sweep of the frequency.

As the frequency approaches the natural frequency of the resonator and sweeps past this frequency the voltage in the resonator will rise from a very low level way off resonance to a high voltage at the resonant frequency and then down to a low level as the frequency passes. This gives rise to two peaks of voltage in the resonator, one while the frequency is increasing and one while the frequency is decreasing. The amplitude of the voltage in the resonator may be determined by means of a simple high frequency diode connected to part of the circuit or to a small loop of a resonant cavity is used.

When the resonator frequency is changed by the presence of moisture the position of these two peaks will change. The difference in frequency between these two peaks is a measure of the reactance in the circuit and is therefore a function of the imaginary component of the dielectric constant. This difference is therefore directly related to the parameter $\epsilon''$. See FIGS. 3A and 3B.

The complex dielectric constant $\epsilon$ may be expressed as follows: $\epsilon = \epsilon' + j\epsilon''$ where $\epsilon'$ is the real component and $\epsilon''$ the imaginary component. $j = (-1)^{1/2}$ or $j = \sqrt{-1}$ Moreover, it has been shown, that for a range of industrial materials the moisture is related to the ratio; $[\epsilon''/(\epsilon'-1)]$ and this function is largely independent of the density. In a number of research reports concerned with the measurement of moisture using microwaves it has been shown that for a large number of materials there is a relationship between the density of the material and the complex dielectric constant at high frequencies. In these materials microwave absorption due to moisture gives rise to a complex dielectric constant $\epsilon=\epsilon'+j\epsilon''$ where $\epsilon'$ and $\epsilon''$ are the parameters of the dielectric contsant $\epsilon$ related to the in phase and quadrature components of the dielectric constant.

The real component is related to the attenuation of a microwave signal or to the reduction in Q factor of a resonator and is relatively easy to measure. It is somewhat more complicated, however, to measure the phase constant, or in the case of a resonator, the small natural change in resonant frequency when the field links with the moist material and the purpose of this application is to describe a very sensitive but simple system for making this measurement which enables a small inexpensive portable instrument to be produced.

The peak voltage reached in the resonator when the frequency sweeps through resonance conveys the information on the Q of the resonator and is related to the parameter $\epsilon'$, the attenuation coefficient. A simple peak reading circuit provides the information on this parameter, alternatively the Q may be determined by the classical method of quadrantal frequency measurement using the width of the peaks at a precise amplitude.

A fast acting comparator, such as a Schmitt trigger circuit, can be adjusted to switch at a point on the waveform in the resonator which is at a voltage of $1/\sqrt{2}$ of the peak voltage. The output of this comparator circuit is in the form of a pulse. This pulse contains all of the information necessary to obtain the two parameters related to the complex dielectric constant. The width of the pulse is a function of the Q of the resonator and therefore of the attenuation coefficient $\epsilon'$ and the time period between the pulse obtained wit increasing frequency which occurred due to the presence of moisture. A block diagram of the system is shown in FIG. 1, discussed at length herein.

The methods by which the information referred to above is extracted from this pulse are standard forms of simple circuitry and the required voltages representing the coefficients of the dielectric constant are easily obtained using either analogue or digital circuitry. The pulse contains the information on both coefficients. The width of the pulse is a direct function of the Q of the tuned circuit and therefore of the energy absorbed by the presence of water linked to the resonator. The time period between the pulses occurring on the positive slope of the frequency characteristic and those occurring on the negative portion of the slope is a function of the moisture content of the material.

What is claimed is:

1. A device for the measurement of moisture in a granular material using high frequency waves, comprising the following:

a. A resonator, the field produced by which interacts with the material to be measured, b. an electromagnetic field directed to pass through the material to be measured, c. a square wave generator cooperatively connected to a triangle wave generator, which in turn emits waves which are generated by a high frequency generator, d. said high frequency generator emitting waves in the range of about 0.5 to about 20 gigahertz, e. means for determining the natural frequency of the resonator and frequency of the resonator in conjunction with the material being tested for moisture content, f. a high frequency diode for measuring the amplitude of voltage output from the resonator with and without material within it, and g. detection means for measuring the frequency shift and height of the peak voltage output of the resonator coupled to with the material being tested.

2. The apparatus of claim 1 further comprising:

h. means for measuring the shift in frequency caused by material having moisture content and material without moisture content.

3. The apparatus of claim 1 further comprising:

i. means for converting the output of the resonator into pulse form.

4. The apparatus of claim 1 wherein the resonator is formed from stripline.

5. The apparatus of claim 1 wherein the resonator is a resonant cavity.

6. The apparatus of claim 5 wherein the material to be tested is placed within the cavity.

7. The apparatus of claim 1 wherein the resonator is a tuned ring.

8. The apparatus of claim 1 wherein the apparatus is further comprised of:

j. calculation means for processing the phase shift and amplitude change of the voltage peak and thereby calculating the moisture of the material to be tested.

9. The method of measuring moisture content in granular materials using microwaves (high frequency waves) comprising the steps of:

a. contacting the material wherein moisture is to be measured with a field produced by a resonator having a natural frequency and said resonator being cooperatively connected to a high frequency generator wherein said high frequency generator produces a frequency which is swept back and forth in a linear manner;

b. said high frequency wave forms being further modulated by a triangle wave generator which sweeps the frequency;

c. said output of said high frequency generator being within the range from about 0.5 to about 20 gigahertz, and wherein said wave forms are modulated to scan back and forth through a pre-determined range of frequency defined by the range of frequency for the moisture to be measured, d. measuring the height of the voltage peaks at resonance with the scanning frequency along wit the time period between the peaks obtained with increasing frequency, and the peaks obtained as the frequency is decreased, and e. determining the parameters of the complex dielectric constant for the material and thereby determining the moisture content of the material utilizing the voltage at resonant frequency.

10. The method of claim 9, further comprising the steps of calculating the time period between the voltage peaks and amplitude of the waves.

11. The method of claim 9 further comprising the step of determining the moisture content of the material independent of the density of the material.

* * * * *